United States Patent [19]

LeRoy

[11] 4,029,097

[45] June 14, 1977

[54] SURGICAL SPONGE COLLECTOR AND DRAINAGE SYSTEM

[75] Inventor: Pierre L. LeRoy, Wilmington, Del.

[73] Assignee: New Research and Development Laboratories, Inc., Wilmington, Del.

[22] Filed: July 25, 1975

[21] Appl. No.: 599,016

[52] U.S. Cl. .................................................. 128/276
[51] Int. Cl.² .......................................... A61M 1/100
[58] Field of Search .............. 206/72, 63.5, 363; 128/276, 277, 278

[56] References Cited

UNITED STATES PATENTS

| | | | |
|---|---|---|---|
| 2,375,643 | 5/1945 | Germanotta | 108/43 X |
| 3,091,858 | 6/1963 | Misicka | 128/276 X |
| 3,349,768 | 10/1967 | Keane | 128/276 |
| 3,520,300 | 7/1970 | Flower | 128/276 |
| 3,841,331 | 10/1974 | Wilder et al. | 128/278 |
| 3,948,390 | 4/1976 | Ferreri | 206/72 |

FOREIGN PATENTS OR APPLICATIONS 847,475  8/1952  Germany .......................... 128/276

Primary Examiner—Hugh R. Chamblee
Assistant Examiner—Wenceslao J. Contreras
Attorney, Agent, or Firm—Connolly and Hutz

[57] ABSTRACT

A surgical sponge collector and drainage system includes a tray having a smooth concave wall contoured for fitting directly against the human body and mounted in contact therewith. The tray includes a perforated shelf disposed below its peripheral rim as a discard area for collecting used sponges and permitting liquid to drain therethrough and ultimately drain to a collector. Aspirating tubes are also provided and inserted into the body at the operation site for withdrawing liquid therefrom into the same collector as from the tray.

16 Claims, 7 Drawing Figures

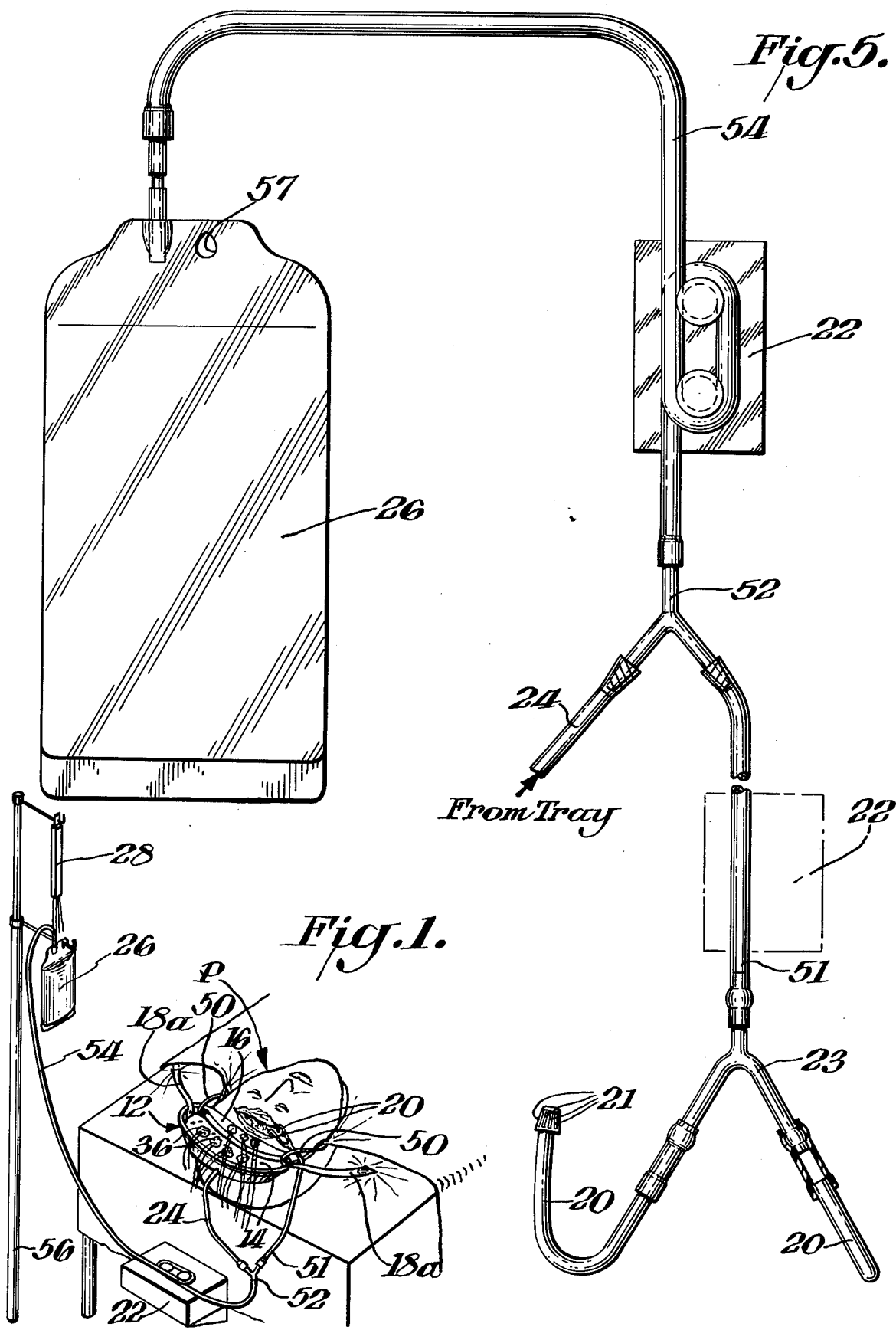

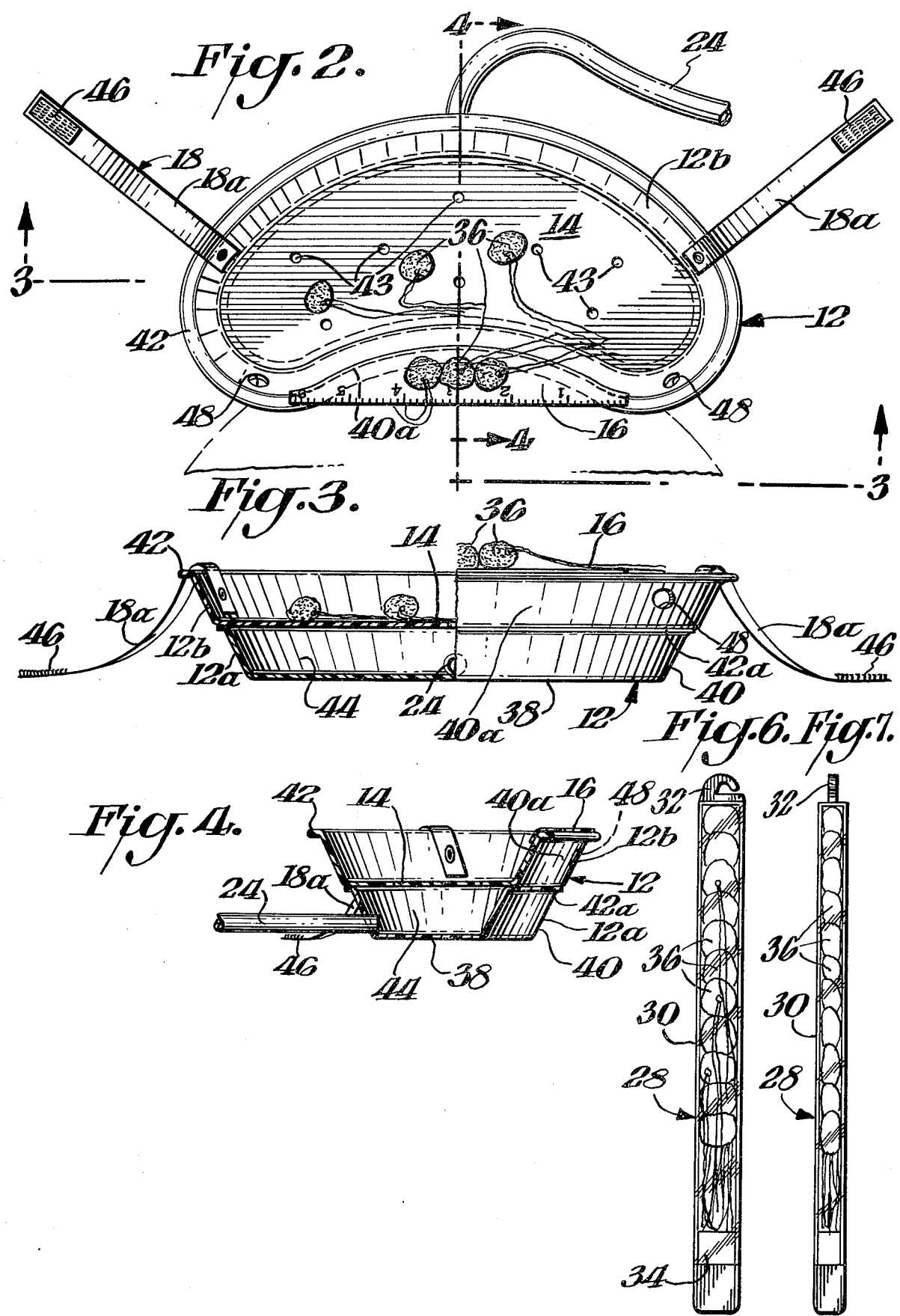

SURGICAL SPONGE COLLECTOR AND DRAINAGE SYSTEM

BACKGROUND OF THE INVENTION

In surgical procedures sponges are used at the operative site. It is necessary that the sponges be conveniently arranged so as to be readily accessible. Obviously such sponges must also be removed from the surgical locus before a wound is closed. To assure that sponges will not be inadvertently left in a wound a count is taken before the operation of the unused sponges and after the operation a count is made of the used sponges and the remaining sponges to assure that all of the sponges have been accounted for. It would be desirable, therefore, to minimize the time required with respect to the sponge handling. There is, therefore, a need for an arrangement which provides a convenient sponge collector readily adaptable not only for collecting used sponges but also for providing the unused sponges in the convenient location as close as possible to the operative site.

In such surgical procedure drainage also presents problems not only with respect to liquid such as saline accumulated by the sponges but also at the operative site itself. There is, therefore, also a need for a convenient and efficient drainage system which can readily be incorporated in standard surgical procedures.

SUMMARY OF THE INVENTION

An object of this invention is to provide a sponge collector and drainage system particularly adapted for surgical uses.

A further object of this invention is to provide such a sponge collector and drainage system which not only incorporates a convenient means for collecting used sponges and the drainage of fluid therefrom but also provides a readily accessible supply of unused sponges.

A still further object of this invention is to provide such a system which includes a drainage means not only for the fluid from the used sponges but also for the fluid directly from the operative site.

In accordance with this invention a surgical sponge collector and drainage system includes a tray having a smooth concave wall contoured for fitting directly against the human body and mounted in contact therewith. The tray includes a discard area in the form of a perforated shelf disposed below its peripheral rim for collecting used sponges and permitting liquid to drain therethrough and ultimately into a collector. Aspirating tubes are also provided and inserted into the body at the operation locus for withdrawing liquid therefrom into the same collector as from the tray.

The sponge collecting tray may be mounted against the body in such a manner as to be suspended therefrom without the necessity of any supporting platform. The discard area or used sponge collecting shelf itself is preferably transparent to provide a visible check of the compartment below the shelf.

In a preferred form of this invention the tray further includes a service area in the form of a second shelf or platform upon which unused sponges may be placed. Advantageously, this platform is calibrated such as with ordinary ruler markings to provide a readily visible indication of the quantity of unused sponges. The platform is disposed over the concave wall portion and is flexible in the event it is necessary to contact the body.

THE DRAWINGS

FIG. 1 is a perspective view showing the novel sponge collection and drainage system of this invention in operation;

FIG. 2 is a plan view of the tray utilized in the sponge collector and drainage system of FIG. 1;

FIGS 3 and 4 are cross-sectional views in elevation taken through FIG 2 along the lines 3—3 and 4—4, respectively;

FIG. 5 is an elevation view of the sponge collection and drainage system illustrated in FIG. 1; and FIGS. 6–7 are front and side elevation views of a sponge dispenser which may be usable with this invention.

DETAILED DESCRIPTION

As shown in FIG. 1 the surgical sponge collector and drainage system 10 comprises a tray 12 having a discard area or shelf 14 upon which used sponges may be placed and having at its top wall a further shelf or platform 16 for unused sponges to comprise a service area. Tray 12 is mounted against the patient P and held in position by suitable fasteners 18 connected in any convenient manner such as, for example, to the patient's gown or to the operating table sheet. System 10 further includes aspirating nozzles 20 which are disposed in the body itself at the operative site. Suitable suction means such as a pump 22 is provided for withdrawing fluid from the operative site. Similarly, a drainage tube 24 communicates with tray 12 to permit fluid to drain from the tray and the fluid from both the aspirating nozzles and the tray is collected in common collector 26.

In use any suitable sponge dispenser 28 would be provided for housing unused sponges. Conventionally, such dispenser would be mounted in the general vicinity of the patient but some distance away therefrom. The mounting of dispenser 28 is schematically illustrated as being from standard 56. In accordance with the practice of this invention at convenient times during an operation a number of unused sponges would be removed from dispenser 28 and placed upon serving area or platform 16. During the course of surgery the unused sponges would become used and accumulate fluid. After being used the sponges would be placed within the tray upon shelf 14 in the discard area. As later described shelf 14 is suitably perforated so that the fluid such as saline would flow from the used sponges to the bottom of container 12 and then be discharged through tube 24 for collection in collector 26.

FIGS. 6–7 illustrate an exemplary form of sponge dispenser. It is to be understood that the details of this dispenser may be widely varied and are described herein for the sake of completeness. As illustrated in FIGS. 6–7, dispenser 28 includes a housing 30 having formed at its upper end a hook 32 or any other suitable mounting means. A dispensing outlet 34 is provided at the bottom thereof so that conventional surgical sponges 36 may be conveniently removed from housing 30.

FIGS. 2–4 show the details of tray 12. As indicated therein, tray 12 includes a bottom wall 38, side walls 40 and peripheral rim 42. One of the side walls 40a has a smooth contour of concave formation for fitting snugly against the body of the patient. Mounted within tray 12 is shelf 14 upon which used sponges may be placed.

The shelf 14 includes any suitable number of perforations 43 so that fluid from the used sponges may flow into the compartment 44 formed between bottom wall 38 and shelf 14. In the preferred form of this invention shelf 14 is transparent to provide ready visibility into compartment 44. The entire tray 12 may also be transparent. Tray 12 may be formed in any suitable manner so as to effectuate the concepts of this invention. For example the tray may be molded in one piece and shelf mounted therein. Alternatively, in the illustrated embodiment the tray includes a lower portion 12a having a peripheral rim 42a upon which an upper portion 12b is secured in any suitable manner. The bottom wall of the upper portion thus forms the shelf 14 itself.

As shown in FIG. 2, a second shelf or platform 16 is disposed beyond the tray proper itself over the concave portion thereof spanning the peripheral rim 42. As later described, platform 16 is made of a flexible material and is provided with calibrations which may, for example, be conventional ruler markings such as inches or centimeters. From experience a surgeon would know quickly from glancing at platform 16 approximately how many any unused sponges 36 are mounted thereon in accordance with the length of the platform taken up by the unused sponges. Accordingly, at suitable times during the operation the amount of unused sponges on platform 16 could be replenished by removing them from dispenser 28.

In the preferred form of this invention in order to minimize space requirements tray 12 is mounted in a suspended or cantilevered fashion directly against the patient. Thus additional table space is not required to support the tray. The suspended mounting is accomplished by suitable fasteners 18. The fasteners 18 may take any appropriate form. For example, as illustrated in FIG. 2 the fasteners comprise traps 18a incorporating velcro 46 or other suitable fastening means which may be used for engagement with velcro on, for example, the patient's gown or the sheet on the operating table.

FIG. 2 illustrates a pair of holes 48 at the front end of tray 12. Holes 48 are provided to accommodate additional fasteners 18. For the sake of clarity these additional fasteners have not been illustrated in FIG. 2. Similar holes also exist to accommodate any number of fasteners 18. The fasteners in front holes 48 may also be of any suitable construction such as straps 18a or may take such forms as conventional towel clamps 50 (FIG. 1) which have a rigid construction and would be connected at any suitable locations at the operative site. The specific details of the fasteners may of course vary in accordance with this invention. The use of such a plurality of fasteners, however, is particularly desirable since the adjustability of these fasteners permits tray 12 to be mounted against the patient and fastened in such a manner that the tray is level so that there will be proper drainage. Accordingly, it is possible to adjust the position of tray 12 with respect to the patient so that, for example, platform 16 will be disposed above the patient. Since platform 16 is made of a flexible material, should it be necessary to lower the tray for secure mounting the platform 16 may contact the patient by yielding or conforming the necessary extent.

As best shown in FIG. 4, a drainage tube 24 communicates with compartment 44 so that the fluid flowing into the compartment will be drained therefrom. Drainage tube 24 may be mounted at any suitable location. In the embodiment illustrated in FIG. 4, tube 24 is juxtaposed bottom wall 38 but enters the tray through the side wall so that the tray will have an unobstructed bottom wall to facilitate storage or mounting on a further support.

System 10 includes further drainage means. For example, as illustrated in FIGS. 1 and 5 this further drainage means includes aspirating nozzles or J-tubes 20 which are inserted into the operative site itself to prevent the accumulation of too much fluid therein. Aspirating nozzles 20 may operate similarly to conventional dental aspirators. Each of the nozzles or J-tubes 20 terminates in a plurality of openings 21. In the illustrated embodiment aspirating nozzles 20 are mounted to Y connector 23 which in turn leads to drainage tube 50 and thence to bifurcated or Y-shaped connector 52 to which drainage tube 24 is also connected. Thereafter the fluid flows through the connector 52 into common drainage tube 54 and ultimately to collector 26. Suction is applied to aspirating nozzles 20 in any suitable manner. This may be accomplished, for example, by means of a conventional pump 22 which is illustrated in FIG. 5 in solid as being mounted to common tube 54. In this form of the invention suction would be applied not only to nozzles 20 but also to compartment 44 in tray 12. If desired, however, pump 22 may be disposed for acting solely upon aspirating nozzles 20 by being located at tube 50 as illustrated in phantom in FIG. 5. As illustrated in FIG. 1, claim 50 severs the additional function of providing a guide for tube 51 of the aspirating unit.

Depending upon the space requirements it may be necessary to mount pump 22 suspended. Accordingly, the pump may be provided with any suitable mounting means for connection to any fixed support such as standard 56 which would be provided for dispenser 28. Similarly, collector 26 should also be mounted in a suspended position and this may be accomplished by likewise mounting the collector to standard 56. As previously noted, standard 56 is illustrated as schematically representative of any suitable support.

As illustrated in FIG. 5, collector 26 may take the form of a transparent bag having calibrations thereon to provide a ready visible indication of the amount of fluid collected therein. Suitable means such as hole 57 is provided in collector 26 for mounting purposes.

Although system 10 is illustrated in its preferred form as being mounted directly in contact with the patient in a suspended manner, the invention may be practiced in its broadest aspect in other manners. For example, if space requirements permit, tray 10 may simply be placed directly upon any suitable support such as the operating table. In such case it would not be necessary to dispose the tray in contact with the patient and thus the tray need not have any particular contour to conform to the patient. It is further possible to utilize compartment 44 as a fluid collector under certain conditions whereby a drainage tube and separate collector would not be necessary. Similarly, the aspirating nozzles might be mounted completely detached from the sponge collecting tray and its components by leading to a separate collector or by leading to the same collector through an independent drainage tube rather than common discharge tube 54. Obviously, other ramifications of this invention may be possible in light of the above teachings.

What is claimed is:

1. A surgical sponge collector and drainage system comprising a tray having a bottom wall and side walls and terminating at its top in a peripheral rim, one of said side walls having a smooth concave contour for fitting against the body of a patient, a flat horizontal shelf in said tray disposed between said bottom wall and said peripheral rim, a fluid-tight closed compartment being between said shelf and said bottom wall, said shelf comprising support means for used sponges, a plurality of perforations in said shelf whereby fluid may drain from said sponges through said shelf and into said compartment formed between said shelf and said bottom wall, strap means on said tray extending laterally beyond said contoured side for urging and maintaining said contoured side in contact with the patient, said strap means comprising the sole fastening means for suspending said tray away from the patient and being supported only at said contoured side in cantilevered fashion, and said strap means being adjustable to provide a means for cantilevered leveling the orientation of said tray.

2. The system of claim 1 including a platform mounted on said peripheral rim of said tray for supporting unused sponges.

3. The system of claim 2 wherein a drainage tube communicates with said compartment for conveying the fluid away therefrom, a fluid collector disposed remote from said tray, and said drainage tube communicating with said fluid collector.

4. The system of claim 3 including aspirating nozzle means for insertion into the patient at the operative site, tube means connected to said nozzle means for conveying fluid from said operative site, suction producing means acting against said tube means for creating a negative pressure in said nozzle means, and said tube means communicating with said collector.

5. The system of claim 2 wherein said platform is substantially horizontal and is calibrated along its length to provide indicating means for the quantity of unused sponges thereon, said platform being made of a flexible material, and said platform being disposed above said contoured side wall and spanning said peripheral rim thereof in the open area formed by said concave contour with said platform being thereby disposed outside said tray without interfering with access to said shelf.

6. A surgical sponge collector and drainage system comprising a tray having a bottom wall and side walls and terminating at its top in a peripheral rim, one of said side walls having a smooth concave contour for fitting against the body of a patient, a shelf in said tray disposed between said bottom wall and said peripheral rim, and shelf comprising support means for used sponges, a plurality of perforations in said shelf whereby fluid may drain from said sponges through said shelf and into a compartment formed between said shelf and said bottom wall, fastening means on said tray for maintaining said contoured side in contact with the patient, said fastening means being adjustable to provide a means for leveling the orientation of said tray, including a platform mounted on said peripheral rim of said tray for supporting unused sponges, a drainage tube communicating with said compartment for conveying the fluid away therefrom, a fluid collector disposed remote from said tray, said drainage tube communicating with said fluid collector including aspirating nozzle means for insertion into the patient at the operative site, tube means connected to said nozzle means for conveying fluid from said operative site, suction producting means acting against said tube means for creating a negative pressure in said nozzle means, said tube means communicating with said collector, said platform being calibrated to provide indicating means for the quantity of unused sponges thereon, said platform being made of a flexible material, said platform being disposed above said contoured side wall and spanning said peripheral rim thereof, and said shelf being transparent to permit visibility into said compartment.

7. The system of claim 6 wherein said fastening means includes four spaced fasteners connected to said tray, and at least one of said fasteners further comprising guide means for said tube means.

8. The system of claim 7 wherein a common drainage tube is connected at one end to said collector, a bifurcated connector being connected to the other end of said common drainage tube, said drainage tube leading from said tray being connected to one leg of said bifurcated connector, said tube means leading from said aspirating nozzles being connected to the other leg of said bifurcated connector, and said collector being calibrated to indicate the amount of fluid therein.

9. A surgical sponge collector and drainage system comprising a tray, said tray having bottom and side walls which terminate in a peripheral rim, a flat horizontal shelf being disposed in said tray between said peripheral rim and said bottom wall for supporting used sponges thereon, a fluid-tight closed compartment being between said shelf and said bottom wall, said shelf having a plurality of perforations to permit fluid to flow through said shelf into said compartment formed between said shelf and said bottom wall, a generally horizontal platform mounted on said peripheral rim for supporting unused sponges thereon, and said platform being displaced laterally beyond said peripheral rim outside of said tray.

10. A surgical sponge collector and drainage system comprising a tray, said tray having bottom and side walls which terminate in a peripheral rim, a shelf being disposed in said tray between said peripheral rim and said bottom wall for supporting used sponges thereon, said shelf having a plurality of perforations to permit fluid to flow through said shelf into a compartment formed between said shelf and said bottom wall, a platform mounted on said peripheral rim for supporting unused sponges thereon, said shelf being transparent, and said platform being calibrated with length indicating indicia thereon.

11. A surgical sponge collector and drainage system comprising a container having a bottom wall and side walls and terminating in a peripheral rim, one of said side walls being adapted for fitting against the body of a patient, said container comprising a compartment for receiving used sponges and fluid, a drainage tube connected to said compartment for draining the fluid therefrom, a collector connected to said drainage tube remote from said compartment, a generally horizontal platform mounted at said peripheral rim at said one side wall, said platform being laterally displaced from said compartment outside said container for holding unused sponges, strap means secured to said container, and said strap means extending laterally beyond said one side wall for mounting said container at the operative site with said one side wall disposed adjacent the patient.

12. The system of claim 11 including aspirating nozzles means for insertion into the body of the patient at the operative site, tube means connected to said aspirating nozzle means, suction producing means acting against said tube means to create a suction in said nozzle means, and said tube means communicating with said collector.

13. The system of claim 11 wherein said container is rigid and self-supporting, and said bottom wall is flat.

14. The system of claim 11 including a flat horizontal perforated shelf in said container below said peripheral rim for supporting used sponges, and calibrations on said platform for visually indicating the amount of sponges thereon.

15. The system of claim 9 wherein one of said side walls is concave for fitting against the patient, and said platform spanning said peripheral rim in the open area formed by said concave contour.

16. The system of claim 9 wherein said bottom wall is flat and horizontal, and said side walls are outwardly inclined.

* * * * *